United States Patent [19]

McDade et al.

[11] Patent Number: 5,342,487
[45] Date of Patent: Aug. 30, 1994

[54] DISTILLATION PROCESS

[75] Inventors: Christine McDade, North Wales; Makarand D. Phadke, Warminister; William D. Weir, Levittown, all of Pa.

[73] Assignee: Rohm and Haas Compnay, Philadelphia, Pa.

[21] Appl. No.: 773,185

[22] Filed: Oct. 8, 1991

[51] Int. Cl.⁵ ............................................. B01D 3/34
[52] U.S. Cl. ................................... 203/6; 203/34; 203/38; 203/DIG. 21; 560/4; 560/218
[58] Field of Search .............. 203/6, 38, 34, DIG. 21, 203/DIG. 6; 560/209, 218, 4

[56] References Cited

U.S. PATENT DOCUMENTS

| | | | |
|---|---|---|---|
| 3,709,928 | 1/1973 | Murayama et al. | 203/8 |
| 3,875,211 | 4/1975 | Steckler | 560/209 |
| 3,988,213 | 10/1976 | Yoshida | 203/9 |
| 4,021,310 | 5/1977 | Shimizu | 203/8 |
| 4,069,242 | 1/1978 | Gurgiolo | 560/209 |
| 4,191,576 | 3/1980 | Fuseya et al. | 430/517 |
| 4,261,798 | 4/1981 | Palmer | 203/9 |
| 4,365,081 | 12/1982 | Shimizu et al. | 560/209 |
| 4,404,395 | 9/1983 | Markiewitz | 560/209 |
| 4,480,116 | 10/1984 | Clonce et al. | 203/8 |
| 4,755,262 | 7/1988 | Matsunaga et al. | 203/DIG. 21 |
| 5,034,156 | 7/1991 | Varwig | 203/8 |

FOREIGN PATENT DOCUMENTS

| | | | |
|---|---|---|---|
| 0134133 | 3/1985 | European Pat. Off. | 560/209 |
| 1137071 | 12/1968 | United Kingdom | 560/209 |
| 1388220 | 12/1972 | United Kingdom . | |

*Primary Examiner*—Virginia Manoharan

[57] ABSTRACT

A process for reducing the amount of unwanted di(-meth)acrylate produced during the distillation of hydroxyalkyl acrylates or hydroxyalkyl methacrylates.

9 Claims, No Drawings

DISTILLATION PROCESS

BACKGROUND OF THE INVENTION

The present invention relates to a process for reducing the amount of alkyleneglycol diacrylate or alkyleneglycol dimethacrylate produced during the distillation of hydroxyalkyl acrylates or hydroxyalkyl methacrylates produced by the metal ion catalyzed esterification of an acrylic or methacrylic acid by an alkylene oxide. The term (meth)acrylate is used herein to describe both acrylate and methacrylate containing compounds or derivatives.

Hydroxyalkyl (meth)acrylates are typically produced by reaction of (meth)acrylic acid with an alkylene oxide in the presence of a metal ion catalyst. Metal ion catalysts include iron salts of organic acids such as iron (meth)acrylate, iron salts of inorganic acids such as ferric chloride, chromium compounds such as chromic or bichromic acid, Lewis acids such as aluminum chloride, as well as organic bases such as tertiary amines and quaternary ammonium salts. Of these metal ion catalysts, iron salts are the most common.

Purification of the hydroxyalkyl (meth)acrylate is generally accomplished by distillation from the crude reaction mixture. One of the major problems with this process is that the hydroxyalkyl (meth)acrylate itself is capable of further esterification with an additional (meth)acrylic acid molecule or transesterification with another hydroxyalkyl (meth)acrylate to produce an alkyleneglycol di(meth)acrylate (hereinafter referred to as "di(meth)acrylate"). The di(meth)acrylate is undesirable because it can act as a crosslinking agent in any subsequent polymerizations in which the hydroxyalkyl (meth)acrylate is a component. Furthermore, the di(meth)acrylate may increase the extent of unwanted polymerization during the distillation step resulting in increased amounts of tars or other unwanted solids in the still bottoms or on the equipment and a corresponding reduction in the yield of the desired hydroxyalkyl (meth)acrylate in the distillate. The extent of formation of this di(meth)acrylate is dependent on the type of catalyst used in the reaction, the concentration of the various reactants, products, or other additives, as well as the distillation conditions. An additional problem that may occur during distillation is that the reaction catalysts normally used often form a variety of side products including complexes with reactants and products in addition to the tars and unwanted solids. These complexes also often interfere with the distillation process.

U.S. Pat. No. 3,709,928 describes the use of polyalkyleneglycols, with higher boiling points than the desired hydroxyalkyl (meth)acrylates, to increase both the purity and overall yield of hydroxyalkyl (meth)acrylates produced by reacting an alkyl (meth)acrylic acid, or its sodium salt, and an alkylene oxide, or corresponding alkyl chlorohydrin, and isolating the product by distillation. The polyalkyleneglycols are reported to have two effects (1), they inhibit the formation of di(meth)acrylate, and (2), they prevent the catalyst used from forming an insoluble solid that interferes with the distillation. However, the exact mechanism of action of the polyalkyleneglycols is not disclosed.

U.S. Pat. No. 4,365,081 describes the preparation of 2-hydroxyalkyl methacrylate by the reaction of methacrylic acid with an alkylene oxide catalyzed by the ferric salt of a variety of carboxylic acids, including (meth)acrylic, fumaric, malic, benzoic, various phthalic, or salicylic. After distillation is complete, addition of water, acetic acid, salicylic acid, ethanolamines or methanol will decompose the distillation residue, which is characterized as an iron containing salt of complex structure. Furthermore, salicylic acid can be added anytime during the reaction or distillation to stabilize the distillation residue.

We approached the problem of di(meth)acrylate production by assuming that the reaction catalyst or catalyst complex also catalyzed the transesterification reaction of hydroxyalkyl (meth)acrylate with itself or its direct esterification with (meth)acrylic acid. Thus, the object of the invention was to discover an additive that would deactivate the catalyst, or catalyst byproducts, thereby avoiding the catalyzed transesterification or direct esterification with resulting di(meth)acrylate contamination of the hydroxyalkyl (meth)acrylate distillate. We have discovered that certain organic compounds have the appropriate mix of physicochemical properties such that they deactivate the catalyst, possibly via some type of sequestering process.

A variety of organic compounds have been found that deactivate the catalyst while minimizing contamination of the product. They share the following properties: a boiling point higher than the product hydroxyalkyl (meth)acrylate, functional groups capable of interacting with the metal cation, and solubility in the reaction mixture. When the boiling point is similar to or less than the product hydroxyalkyl (meth)acrylate, it is difficult to avoid contamination of the distillate with the additive.

Furthermore, the additive should preferably be a weaker acid than (meth)acrylic acid. We have found that when the additive's $pK_a$ is too low any unreacted (meth)acrylic acid that may have complexed with the metallic catalyst is liberated resulting in an increased (meth)acrylic acid level in the distillate. The mix of properties may be varied depending on the particular hydroxyalkyl (meth)acrylate being produced.

Additives found to substantially reduce di(meth)acrylate formation include, for example, the following: stearic acid, lauric acid, octanoic acid, p-toluic acid, phenylacetic acid, adipic acid, o-phthalic acid, succinic acid, citric acid, 2-hydroxyphenylacetic acid, phthalic anhydride, succinic anhydride, diglycolic anhydride, catechol, 3-methoxycatechol, 2-hydroxybenzyl alcohol, polyacrylic acids, and glycerol.

Preferred additives include the long chain fatty acids (e.g. stearic and lauric acids) and the diols (catechol, 3-methoxycatechol, and glycerol). Most preferred is catechol. The effective amount of additive is the amount required to reduce the di(meth)acrylate level in the distillate below that found in the absence of the additive. It may range from about 0.1 to about 5 weight percent. However, from about 0.5 to about 2.0 weight percent is preferred, and from about 0.75 to about 1.0 weight percent is most preferred.

DETAILED DESCRIPTION OF THE INVENTION

This invention is directed to a method for reducing formation of di(meth)acrylate during the distillation of hydroxyalkyl (meth)acrylates from the iron catalyzed reaction of (meth)acrylic acids with alkylene oxides by conducting the distillation in the presence of a catalyst deactivating additive preferably by admixing to the reaction mixture before beginning the distillation an effective amount of one or more of a catalyst deactivating additive selected from:

a. substituted or unsubstituted $C_4$–$C_{20}$alkyl or $C_7$–$C_{20}$aralkyl mono-, di-, or tricarboxylic acids, anhydrides of the mono-, di-, or tricarboxylic acids, or mixed anhydrides of the mono-, di, or tricarboxylic acids wherein the substituent is selected from one to four $C_1$–$C_4$alkoxy such as methoxy, ethoxy, propoxy, or butoxy, $C_1$–$C_4$alkyl such as methyl, ethyl, propyl, or butyl, halo such as chloro, bromo, fluoro, or aryl such as phenyl, or naphthyl; examples of these acids are stearic, lauric, octanoic, phenylacetic, adipic, succinic, and the like; preferred acids are stearic, lauric, phenylacetic and the like; most preferred are stearic, lauric, and the like acids. Examples of anhydrides of the mono, di, or tricarboxylic acids are succinic, and the like;

b. substituted aryl mono-, di-, or tricarboxylic acids, anhydrides of the mono-, di-, or tricarboxylic acids, or mixed anhydrides of the mono-, di-, or tricarboxylic acids wherein the substituent is selected from one to four $C_1$–$C_4$ alkoxy such as methoxy, ethoxy, propoxy, or butoxy, $C_1$–$C_4$ alkyl such as methyl, ethyl, propyl, or butyl, halo such as chloro, bromo, fluoro, or aryl such as phenyl, or naphthyl; examples of the acids are p-toluic, o-phthalic, and the like; preferred acids are o-toluic and the like; examples of the anhydrides are phthalic and the like;

c. substituted or unsubstituted $C_3$–$C_{10}$vicinal diols wherein the substituent is selected from one to four $C_1$–$C_4$ alkoxy such as methoxy, ethoxy, propoxy, butoxy, and the like, $C_1$–$C_4$ alkyl such as methyl, ethyl, propyl, butyl, and the like, halo such as chloro, bromo, fluoro, and the like, or aryl such as phenyl, and the like; examples of these diols include glycerol and the like;

d. substituted or unsubstituted o-substituted phenols wherein the o-substituted substituent is selected from hydroxy, hydroxymethyl, or carboxymethyl, and, when substituted, the substituent is selected from one to four $C_1$–$C_4$ alkoxy such as methoxy, ethoxy, propoxy, butoxy, and the like, $C_1$–$C_4$ alkyl such as methyl, ethyl, propyl, butyl, and the like, halo such as chloro, bromo, fluoro, and the like, or aryl such and phenyl and the like; examples of these o-substituted phenols include 2-hydroxyphenylacetic acid, catechol, 3-methoxycatechol, 2-hydroxybenzyl alcohol, and the like; preferred o-substituted phenols are 2-hydroxyphenylacetic acid, catechol, and the like; most preferred is catechol and the like;

e. substituted or unsubstituted o-substituted polyaromatic alcohols wherein the substituent is selected from one to four $C_1$–$C_4$ alkoxy such as methoxy, ethoxy, propoxy, butoxy, and the like, $C_1$–$C_4$alkyl such as methyl, ethyl, propyl, butyl, and the like, halo such as chloro, bromo, fluoro, and the like, or aryl such and phenyl and the like, and wherein the o-substituent is selected from hydroxy, hydroxymethyl, carboxy, or carboxymethyl; examples of these o-substituted polyaromatic alcohols include 2,3-dihydroxynaphthalene and the like;

f. substituted or unsubstituted diglycolic anhydrides wherein the substituent is selected from one to four $C_1$–$C_4$ alkoxy such as methoxy, ethoxy, propoxy, butoxy, and the like, $C_1$–$C_4$ alkyl such as methyl, ethyl, propyl, butyl, and the like, halo such as chloro, bromo, fluoro, and the like, or aryl such as phenyl and the like; examples include diglycolic anhydride and the like;

g. poly(meth)acrylic acids and the like; examples include polyacrylic acid and the like.

The rationale for the approach used in this invention was to minimize the effectiveness of iron containing process catalysts as di(meth)acrylate production catalysts during the processing of crude hydroxyalkyl (meth)acrylate. Additives can be mixed with crude hydroxyalkyl (meth)acrylate at levels up to about five percent by weight with the pure hydroxyalkyl (meth)acrylate typically isolated by distillation. Effectiveness of the additives varies depending on their particular physicochemical properties, properties of the reactant (meth)acrylic acid and epoxide, as well as the product hydroxyalkyl (meth)acrylate. Two different, but related, modes of deactivation may be at work in this process. Certain of the additives, notably the long-chain fatty acids (stearic and lauric), produce an insoluble material resembling a tar. This insoluble material sequesters the catalyst in such a way that it can no longer catalyze di(meth)acrylate production. Removal of the insoluble material by filtration followed by distillation of the mother liquor results in a high recovery of hydroxyalkyl (meth)acrylate with significantly reduced di(meth)acrylate content. This result also confirms that it is the catalyst that has a major contribution in formation of the di(meth)acrylate. With other additives tars are not produced. However, the catalyst is nonetheless deactivated because again, distillation results in a high recovery of hydroxyalkyl (meth)acrylate with reduced di(meth)acrylate.

The following examples and comparative examples illustrate the present invention more specifically. The invention is in no way limited to these specific examples.

EXAMPLES

A model hydroxyalkyl (meth)acrylate production system was chosen for purposes of determining the effectiveness of each additive in reducing di(meth)acrylate content in distilled product. In this system, undistilled crude hydroxyethyl acrylate produced from the iron catalyzed esterification of acrylic acid and ethylene oxide was treated with varying amounts of each additive and the resulting mixture evaluated. The crude hydroxyethyl acrylate used in these studies contained approximately 3000 ppm of iron.

The primary evaluation procedure, referred to as "bottle studies" for the determination of di(meth)acrylate formation, involved heating reaction mixtures in closed 2 oz. bottles at 80° C. for periods of 3 or 6 hours. This procedure was used to highlight differences in di(meth)acrylate formation between untreated reaction crude and reaction crude that was treated with an additive. A secondary evaluation involved laboratory distillation of the reaction crude with and without the additive. The results of these studies are summarized in Tables 1 and 2.

Examples 1–43 were conducted using the bottle study evaluation as follows:

The additive was added to the hydroxyethyl acrylate reaction crude containing up to 0.5 weight percent di(meth)acrylate. The mixture was heated at 80° C. for either three or six hours. The di(meth)acrylate content of the mixture was then determined by HPLC analysis. The di(meth)acrylate content of the mixture was compared to that in a sample treated identically except for the absence of the additive. Table 1 summarizes the results of these experiments.

TABLE 1

| Example No. | Additive | Weight % | Conditions[1] | Ratio[2] |
|---|---|---|---|---|
| 1 | Stearic acid | 2.0 | A-1 | 0.6–0.7[3] |
| 2 | Lauric acid | 0.2 | A-1 | 0.4 |
| 3 | Lauric acid | 2.0 | A-1 | 0.2 |
| 4 | Octanoic acid | 2.0 | A-1 | 0.8 |
| 5 | p-Toluic acid | 2.0 | B-1 | 0.5 |
| 6 | Phenylacetic acid | 2.0 | A-1 | 0.6 |
| 7 | Adipic acid | 2.0 | A-1 | 0.5 |
| 8 | o-Phthalic acid | 1.0 | C-2 | 0.5 |
| 9 | o-Phthalic acid | 2.0 | A-1 | 0.6 |
| 10 | Succinic acid | 0.5 | B-1 | 0.8 |
| 11 | Succinic acid | 1.0 | B-2 | 0.5 |
| 12 | Succinic acid | 2.0 | A-2/B-2 | 0.3–0.7 |
| 13 | Salicylic acid[4] | 0.5 | A-2/B-2 | 0.7–1.1 |
| 14 | Salicylic acid[4] | 1.0 | A-2 | 1.1 |
| 15 | Salicylic acid[4] | 1.5 | A-2 | 1.2 |
| 16 | Salicylic acid[4] | 2.0 | A-2/B-2 | 0.6–1.0 |
| 17 | Salicylic acid[4] | 2.2 | A-1 | 0.8–0.9 |
| 18 | Salicylic acid[4] | 5.0 | B-2 | 0.6 |
| 19 | 2-Hydroxyphenylacetic acid | 1.0 | A-1 | 0.8 |
| 20 | Phthalic anhy. | 2.0 | B-1 | 0.6 |
| 21 | Succinic anhy. | 2.0 | B-1 | 0.8 |
| 22 | Succinic anhy. | 2.5 | A-2 | 0.4 |
| 23 | Diglycolic anhy. | 1.0 | A-2 | 0.8 |
| 24 | Catechol | 0.5 | A-1 | 0.6 |
| 25 | Catechol | 1.0 | A-1 | 0.4–0.6 |
| 26 | Catechol | 2.0 | A-1/B-1 | 0.4–0.6 |
| 27 | 3-Methoxycatechol | 1.0 | B-2 | 0.6 |
| 28 | 2-Hydroxybenzyl alcohol | 1.0 | B-1 | 0.7 |
| 29 | Polyacrylic acid | 0.5 | B-2 | 0.7 |
| 30 | Polyacrylic acid | 2.0 | B-2 | 0.6 |
| 31 | Glycerol | 0.5 | B-1 | 0.9 |
| 32 | Glycerol | 1.0 | B-1 | 0.8 |
| 33 | Glycerol | 2.0 | A-2/B-1 | 0.6–0.8 |
| 34 | Polyethylene glycol (PEG) MW of 150[4] | 0.5 | B-2 | 1.8 |
| 35 | PEG 200[4] | 0.5 | B-2 | 0.7 |
| 36 | PEG 200[4] | 2.0 | A-1 | 0.9 |
| 37 | PEG 400[4] | 0.5 | B-1/B-2 | 0.9–1.0 |
| 38 | PEG 600[4] | 0.5 | B-2 | 0.8 |
| 39 | PEG 1000[4] | 0.5 | B-2 | 0.7 |
| 40 | PEG 1000[4] | 1.0 | A-1 | 1.2 |
| 41 | PEG 2000[4] | 2.0 | A-1 | 0.9 |
| 42[5] | Lauric acid | 1.0 | A-1 | 0.7 |
| 43[5] | Catechol | 1.0 | A-1 | 0.8–0.9 |

[1]Initial di(meth)acrylate concentration:
A = Less than 0.3 weight percent
B = 0.3 weight percent or more
C = Unknown initial concentration
−1 = 80° C. for 6 hours
−2 = 80° C. for 3 hours
[2]Ratio of final di(meth)acrylate concentration - additive vs. no additive
[3]A range indicates results of multiple experiments, not necessarily under identical conditions
[4]Comparative example
[5]Hydroxyethyl methacrylate crude used in this experiment; ratio was based on concentrations of ethyleneglycol dimethacrylate Examples 44–56 were conducted by vacuum distillation of crude reaction mixture under laboratory conditions. The distillation was completed in either 1–2 hours or 5–6 hours in order to simulate short-term and long-term distillations. The concentration of di(meth)acrylate in the distillate from the sample containing additive was then compared to that in a similar sample without additive. The results of these experiments are summarized in Table 2.

TABLE 2

| Example # | Additive | Weight % | Conditions[1] | Ratio[2] |
|---|---|---|---|---|
| 44 | Lauric acid | 0.5 | A-2 | 1.0 |
| 45 | Lauric acid | 2.0 | A-1/A-2 | 0.03–0.7[3] |
| 46 | Phthalic acid | 0.5 | A-2 | 0.7 |
| 47 | Phthalic acid | 2.0 | A-2 | 0.3 |
| 48 | Phenylacetic acid | 2.0 | A-2 | 0.6 |
| 49 | Salicylic acid[4] | 0.5 | A-2 | 0.7 |
| 50 | p-Toluic acid | 0.5 | A-2 | 1.1 |
| 51 | p-Toluic acid | 2.0 | A-2 | 0.5 |
| 52 | Polypropylene glycol | 2.0 | A-2 | 1.0 |
| 53 | Glycerol | 2.0 | A-2 | 1.0 |
| 54 | Succinic acid | 2.0 | B-2 | 0.3 |
| 55 | Catechol | 1.0 | A-2/B-2 | 0.2–0.4 |
| 56 | Catechol | 2.0 | B-2 | 0.2 |

[1]Initial di(meth)acrylate concentration:
A = Less than 0.3 weight percent
B = 0.3 weight percent or more
−1 = 1-2 hour distillation time
−2 = 5-6 hour distillation time
[2]Ratio of final di(meth)acrylate concentration (less initial concentration) -additive vs. no additive
[3]A range indicates results of multiple experiments, not necessarily under identical conditions
[4]Comparative example A range indicates results of multiple experiments, not necessarily under identical conditions Comparative example

We claim:

1. A method comprising reducing formation of diacrylates or dimethacrylates during the distillation of hydroxylakyl acrylates or hydroxyalkyl methacrylates from a reaction mixture produced by the iron catalyzed reaction of an acrylic or a methacrylic acid with an alkylene oxide by conducting the distillation in the presence of an amount of from about 1 to about 5 weight percent consisting essentially of at least one of a catalyst deactivating additive selected from:

a. substituted or unsubstituted $C_4$–$C_{20}$ alkyl or $C_7$–$C_{20}$ aralkyl mono-, di-, or tricarboxylic acids, anhydrides of the mono, di, or tricarboxylic acids or mixed anhydrides of the mono, di, or tricarboxylic acids, wherein the substituent is selected from one to four $C_1$–$C_4$ alkoxy, $C_1$–$C_4$ alkyl, halo, or aryl;

b. substituted $C_6$–$C_{10}$ aryl mono, di-, or tricarboxylic adds, anhydrides of the mono, di, or tricarboxylic acids, or mixed anhydrides of the mono, di, or tricarboxylic acids, wherein the substituent is selected from $C_1$–$C_4$ alkoxy, $C_1$–$C_4$ alkyl, halo or aryl;

c. substituted or unsubstituted $C_3$–$C_{10}$ vicinal diols, wherein the substituent is selected from one to four hydroxy, $C_1$–$C_4$ alkoxy, $C_1$–$C_4$ alkyl, halo, or aryl;

d. substituted or unsubstituted o-substituted phenols wherein the substituent is selected from one to four $C_1$–$C_4$ alkoxy, $C_1$–$C_4$ alkyl, halo, or aryl, and wherein the o-substituent is selected from hydroxy, hydroxymethyl, or carboxymethyl;

e. substituted or unsubstituted o-substituted polyaromatic alcohols wherein the substituent is selected from one to four $C_1$–$C_4$ alkoxy, $C_1$–$C_4$ alkyl, halo, or aryl, and wherein the o-substituent is selected from hydroxy, hydroxymethyl, carboxy, or carboxymethyl;

f. substituted or unsubstituted diglycolic anhydrides wherein the substituent is selected from one to four $C_1$–$C_4$ alkoxy, $C_1$–$C_4$ alkyl, halo, or aryl; and, g. polyacrylic acids.

2. The method of claim 1 wherein the additive is added prior to the distillation.

3. The method of claim 3, wherein the additive is admixed in the amount of from about 2 to about 5 weight percent.

4. The method of claim 1 wherein the additive is selected from substituted or unsubstituted $C_4$–$C_{20}$ monocarboxylic acids, anhydrides of the monocarboxylic acids, mixed anhydrides of the monocarboxylic acids, wherein the substituent is selected from one to four $C_1$–$C_4$ alkoxy, $C_1$–$C_4$ alkyl, halo, or aryl groups, and substituted or unsubstituted o-substituted phenols, wherein the o-substituent is selected from hydroxy, hydroxymethyl, and carboxymethyl, wherein the substituent is selected from one to four $C_1$–$C_4$ alkoxy, $C_1$–$C_4$ alkyl, halo, or aryl groups.

5. The method of claim 6, wherein the monocarboxylic acid is selected from stearic acid or lauric acid.

6. The method of claim 4, wherein the o-substituted phenol is catechol or 3-methoxycatechol.

7. The method of claim 6 wherein the hydroxyalkyl acrylate is hydroxyethyl acrylate.

8. The method of claim 1 wherein insoluble materials present the reaction mixture after admixing the additive are removed prior to distillation.

9. The method of claim 1 wherein the hydroxyalkyl acrylate is hydroxyethyl acrylate.

* * * * *